United States Patent [19]
O'Lenick, Jr.

[11] Patent Number: 4,958,032
[45] Date of Patent: Sep. 18, 1990

[54] N-ALKOXYLATED ETHER 2-PYRROLIDONES

[76] Inventor: Anthony J. O'Lenick, Jr., 743 Ridgeview Dr., Lilburn, Ga. 30247

[21] Appl. No.: 333,539

[22] Filed: Apr. 5, 1989

[51] Int. Cl.$^5$ .......................................... C07D 207/27
[52] U.S. Cl. ...................................... 548/543; 424/70; 427/389.9; 540/485; 546/290
[58] Field of Search ......................................... 548/543

[56] References Cited

U.S. PATENT DOCUMENTS

| | | | |
|---|---|---|---|
| 4,122,170 | 10/1978 | Rajadhyaksha | 424/180 |
| 4,316,893 | 2/1982 | Rajadhyaksha | 424/180 |
| 4,405,616 | 9/1983 | Rajadhyaksha | 424/244 |
| 4,422,970 | 12/1983 | Rajadyaksha | 260/239.3 R |
| 4,423,040 | 12/9183 | Rajadhyaksha | |
| 4,424,210 | 1/1984 | Rajadhyaksha | 424/180 |
| 4,444,762 | 4/1984 | Rajadhyaksha | 424/180 |
| 4,461,638 | 7/1984 | Rajadhyaksha | 71/27 |
| 4,525,199 | 1/1985 | Rajadhyaksha | 514/788 |
| 4,562,075 | 12/1985 | Rajadhyaksha | 514/788 |
| 4,762,522 | 8/1988 | Maue | 8/94.19 R |
| 4,775,527 | 10/1988 | Bires | 424/62 |
| 4,793,994 | 10/1988 | Helioff | 424/71 |

*Primary Examiner*—David B. Springer

[57] ABSTRACT

The present invention deals with the composition, and application of novel alkoxylated ether containing lactam compounds, useful as surface active agents. Compounds of this invention have emulsification, wetting, softening, anti-tangle, conditioning, complexation and solubilization properties.

The compounds of the current invention conform to the following structure;

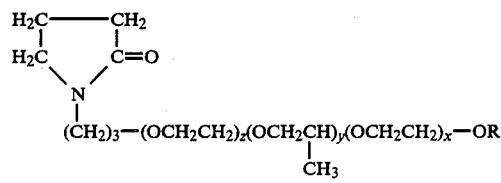

wherein;
R is an alkyl having from 10 to 36 carbon atoms;
x, y and z are independently integers from 0 to 50, with the proviso that the sum of x+y+z be greater than zero.

7 Claims, No Drawings

N-ALKOXYLATED ETHER 2-PYRROLIDONES

BACKGROUND OF THE INVENTION

1. Field of the Invention

The present invention deals with the composition, and application of novel alkoxylated ether containing lactam compounds, useful as surface active agents. Compounds of this invention have emulsification, wetting, softening, anti-tangle, conditioning, ability to complex and solubilization properties. The presence of ethylene and propylene oxide in the molecule backbone results in an inverse cloud point. This property allows the formulator to get minimum solubility and maximum substantivity at higher use temperatures, and more solubility and lesser substantivity at lower temperature.

2. Description of the Art Practices

The reaction of aliphatic primary amines with butyrolactone is well known to those skilled in the art and is disclosed in various publications and a series of patents by Rajadhyaksha, including U.S. Pat. No. 4,423,040 issued Dec. 27, 1983, which teaches that 1-substituted azacyclohexan-2-ones can be prepared and used as physiologically active agents. Related patents to Rajadhyaksha include U.S. Pat. Nos. 4,525,199; 4,461,638; 4,444,762; 4,562,075; 4,316,893; 4,122,170; 4,405,616; and 4,415,563. Since there are no ether nor alokoxylate groups in the disclosed compounds, none of the referenced patents teach the compounds of the present invention.

Lower alkyl pyrrolidones have found applications as low toxicity aprotic solvents. However the absence of a hydrophobe on the molecule make the lower alkyl products non-surface active.

OBJECT OF THE INVENTION

One aspect of this invention relates to a particular group on alkoxylated ether containing N substituted lactams and novel properties of these materials. An additional aspect of the invention is the application of these materials as surface active agents in specific fields were the alkoxylated ether linkages give superior functional attributes. One additional aspect of the invention relates to the incorporation of a regiospecific beta branched ether amine based upon guerbet alcohols into the ether lactam. As will become apparent, the liquidity and high molecular weight of the guerbet moiety, makes these products well suited for applications like personal care were low irritation and substantivity is important.

Another aspect of the invention is to provide products which have an inverse cloud point in aqueous solution. The inverse cloud point phenomena which occurs as one heats an aqueous solution to a critical temperature has been well documented. More detailed descriptions of this are found in standard textbooks, such as A. M. Schwartz and J. W. Perry "Surface Active Agents", Vol. I (1949); and "Surface Active Agents and Detergents" Vol. II (1958). Interscience Publishers, New York, the descriptions of which are incorporated herein by reference.

The presence of ethylene and propylene oxide in the molecule backbone results in an inverse cloud point. This property allows the formulator to get minimum solubility and maximum substantivity at higher use temperatures, and more solubility and lesser substantivity at lower temperature.

THE INVENTION

The compounds of the current invention conform to the following structure;

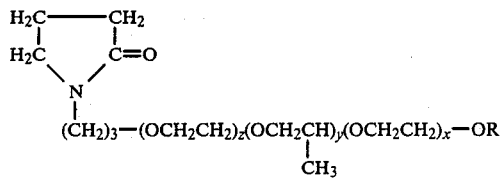

wherein R is a alkyl having from 10 to 36 carbon atoms and n is 1.

The cyclic nature of these compounds, the presence of the ether linkage, the degree of alkoxylation, mole ratio of ethylene oxide to propylene oxide, and the hydrophobic nature of the "R" group taken together result in maximum efficiency and flexibility of properties as surface active agents. The critical micelle concentration, i.e. the concentration at which micelles begin to form are very low for these materials (approx. concentration of $5 \times 10^{-5}$).

The resonance forms of the lactam and the hydrogen bonding which results from the presence of the alkoxylate group in water, results in unique properties. The resonance forms and the electronegative ether linkage taken together result in a high dipole moment and enhanced complexation capabilities. The added hydrogen bonding of the ethylene oxide and propylene oxide groups also increases the complexation ability and renders upon the molecule the property of an inverse cloud point, the significance of which will become apparant.

The compounds of this invention can be tailored to specific applications by the selecting the proper "R" group, the degree of alkoxylation, and the relative amounts of ethylene oxide and propylene oxide present in the molecule. These factors comes from the amine compound chosen to be reacted with butyrolactone.

The preparation of the alkoxylated ether amines are known to those skilled in the art and are items of commerce marketed by Tomah Products. The technology is summarized by the following equation;

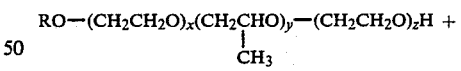

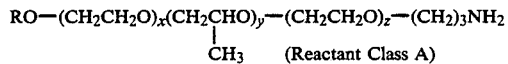

One specific group of ether amines, commercially available from Tomah Products, useful in the preparation of the compounds of this invention are alkoxylated Guerbet Alcohols. These regiospecifically beta branched alcohols have been known since the 1890's when Marcel Guerbet first synthesized them. (M. Guerbet, C. R. Acad. Sci. Paris, 128, 511; 1002 (1899)). These materials are high in molecular weight and are liquid to very low temperatures. The guerbet reaction gives very specific branching in the alcohol as shown;

$$2\ CH_3(CH_2)_9-OH \longrightarrow CH_3(CH_2)_7\overset{\underset{\displaystyle |}{(CH_2)_9CH_3}}{C}HCH_2-OH + HOH\uparrow$$

As can be seen by the above reaction the molecules have substitution on the second carbon from the hydroxyl group. This branching has been found to be critical to the preparation of a product having the desired properties. If the branching were on the same carbon as the hydroxyl group, the hydroxyl group would be a secondary one and would be very hindered and has low reactivity. As one moves the branch position away from the beta carbon, the liquidity, and substantivity to hair and fiber decreases.

Guerbet alcohols that are the reaction product of one specific raw material alcohol will result in a so called "homo-guerbet". In this case R' and R" are identical. If the starting alcohols used in the guerbet reaction are of differing molecular weights a so called "hetero-guerbet" results. This type of guerbet has a mixed distribution of all possible combinations of alcohols. For this reason R and R' in the generic formula may be the same or different.

$$\underset{\text{Heteroguerbet}}{R'\overset{\underset{\displaystyle |}{R''}}{C}HCH_2OH} \qquad \underset{\text{Homoguerbet}}{R''\overset{\underset{\displaystyle |}{R''}}{C}HCH_2OH}$$

The use of guerbet derived ether amines to prepare compounds of this invention results in substantive liquid products. The high molecular weight of the hydrophobe allows for better oil solubilization using these surfactants over conventional nonionic surfactants.

EXAMPLES

Raw Material Examples

Reactant A

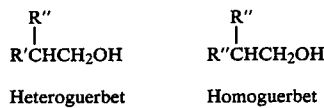

$$RO-(CH_2CH_2O)_x(CH_2\overset{\underset{\displaystyle |}{CH_3}}{C}HO)_y-(CH_2CH_2O)_z(CH_2)_3NH_2$$

| Example | R | x | y | z |
|---|---|---|---|---|
| A | $C_{10}H_{21}$ | 0 | 4 | 2 |
| B | $C_{18}H_{38}$ | 2 | 2 | 2 |
| C | $C_{20}H_{42}$ | 0 | 0 | 6 |
| D | $C_{16}H_{34}$ | 0 | 6 | 0 |
| E | $C_{18}=H_{36}$ | 0 | 6 | 4 |
| F | $C_{10}H_{21}$ | 3 | 6 | 3 |
| G | $C_{18}H_{34}$ | 0 | 3 | 0 |
| H | $C_{18}H_{34}$ | 6 | 0 | 0 |
| I | $C_{18}H_{34}$ | 1 | 1 | 1 |

Guerbet Alcohol Alkoxylated Ether Amines

$$R = R'\overset{\underset{\displaystyle |}{R''}}{C}HCH_2-$$

| Example | R' | R" | x | y | z |
|---|---|---|---|---|---|
| J | $C_8$ | $C_{10}$ | 0 | 0 | 0 |
| K | $C_8$ | $C_{10}$ | 1 | 1 | 1 |
| L | $C_8$ | $C_{10}$ | 0 | 5 | 2 |
| M | $C_8$ | $C_{10}$ | 5 | 5 | 5 |
| N | $C_8$ | $C_{10}$ | 10 | 10 | 10 |
| O | $C_{11}$ | $C_{13}$ | 0 | 0 | 0 |
| P | $C_{11}$ | $C_{13}$ | 1 | 1 | 1 |
| Q | $C_{11}$ | $C_{13}$ | 0 | 5 | 2 |
| R | $C_{11}$ | $C_{13}$ | 5 | 5 | 5 |
| S | $C_{11}$ | $C_{13}$ | 10 | 10 | 10 |
| T | $C_{16}$ | $C_{18}$ | 0 | 0 | 0 |
| U | $C_{16}$ | $C_{18}$ | 1 | 1 | 1 |
| V | $C_{16}$ | $C_{18}$ | 0 | 5 | 2 |
| W | $C_{16}$ | $C_{18}$ | 5 | 5 | 5 |
| X | $C_{16}$ | $C_{18}$ | 10 | 10 | 10 |

The following are suggested embodiments of present invention.

General Reaction Procedure #1 (Autoclave)

Into a stainless autoclave was introduced 214.0 grams of $CH_3-(CH_2)_{11}-O-(CH_2)_3-NH_2$ and 95.0 grams of butyrolactone. The autoclave was sealed and 100 psig nitrogen was applied. The contents were heated to 275° C. and held for eight hours, during which time the pressure rose to about 480 psig. The reaction product was distilled to give a product which conformed to the following generic structure;

$$\begin{array}{c}H_2C-CH_2\\ | \quad\quad |\\ H_2C \quad\ C=O\\ \diagdown\ \diagup\\ N\\ |\\ (CH_2)_3-(OCH_2CH_2)_z(OCH_2\overset{\underset{\displaystyle |}{CH_3}}{C}H)_y(OCH_2CH_2)_xO-R\end{array}$$

| Example Number | Reactant A ether amine alkoxylate |
|---|---|
| 1 | 539.0 Grams Example A |
| 2 | 622.0 Grams Example B |
| 3 | 602.0 Grams Example C |
| 4 | 654.0 Grams Example D |
| 5 | 856.0 Grams Example E |
| 6 | 833.0 Grams Example F |
| 7 | 505.0 Grams Example G |
| 8 | 592.0 Grams Example H |
| 9 | 435.0 Grams Example I |
| 10 | 383.0 Grams Example J |
| 11 | 486.0 Grams Example K |
| 12 | 766.0 Grams Example L |
| 13 | 1118.0 Grams Example M |
| 14 | 1413.0 Grams Example N |
| 15 | 48.50 Grams Example O |
| 16 | 632.0 Grams Example P |
| 17 | 868.0 Grams Example Q |

| Example Number | Reactant A ether amine alkoxylate |
|---|---|
| 18 | 1220.0 Grams Example R |
| 19 | 1955.0 Grams Example S |
| 20 | 624.0 Grams Example T |
| 21 | 771.0 Grams Example U |
| 22 | 1007.0 Grams Example V |
| 23 | 1799.0 Grams Example W |

General Reaction Procedure #2 (Atmospheric)

Introduce into a glass flask the specified number of grams of Reactant A and 150.0 grams of butyrolactone. The contents of the flask are then heated to 75° C. and held for eight hours. Subsequently, the temperature was raised to 250° C. slowly over 4 hours. Then vacuum was applied and the reaction product was distilled to give a product which conformed to the following generic structure;

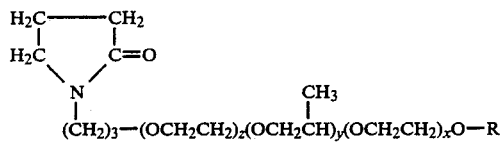

| Example Number | Reactant A ether amine alkoxylate |
|---|---|
| 24 | 539.0 Grams Example A |
| 25 | 622.0 Grams Example B |
| 26 | 602.0 Grams Example C |
| 27 | 654.0 Grams Example D |
| 28 | 856.0 Grams Example E |
| 29 | 833.0 Grams Example F |
| 30 | 505.0 Grams Example G |
| 31 | 592.0 Grams Example H |
| 32 | 435.0 Grams Example I |
| 33 | 383.0 Grams Example J |
| 34 | 486.0 Grams Example K |
| 35 | 766.0 Grams Example L |
| 36 | 1118.0 Grams Example M |
| 37 | 1413.0 Grams Example N |
| 38 | 485.0 Grams Example O |
| 39 | 632.0 Grams Example P |
| 40 | 868.0 Grams Example Q |
| 41 | 1220.0 Grams Example R |
| 42 | 1955.0 Grams Example S |
| 43 | 624.0 Grams |

| Example Number | Reactant A ether amine alkoxylate |
|---|---|
|  | Example T |
| 44 | 771.0 Grams Example U |
| 45 | 1007.0 Grams Example V |
| 46 | 1799.0 Grams Example W |
| 47 | 2094.0 Grams Example X |

APPLICATIONS

Wet Comb Out Test

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12-14 seconds.

| Rinse Conditioner (Wet Comb Out Test) | |
|---|---|
| Product | Time in Seconds |
| Product Example #17 | 12 |
| Product Example #33 | 14 |
| Stearyldimethylbenzyl ammonium chloride | 12 |

As can be seen, the compounds of the invention give significant conditioning properties to hair, and coupled with their mild nature with regard to skin and eyes, makes it a prime candidate for cosmetic applications.

What is claimed is:

1. A substituted lactam conforming to the following formula;

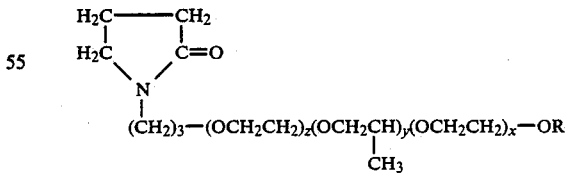

wherein;

R is a alkyl having from 10 to 36 carbon atoms;

x, y and z are independently integers from 0 to 50, with the proviso that the sum of $x+y+z$ be greater than zero.

2. A compound of claim 1 wherein R has 12 to 30 carbon atoms, and x, y and z are independently integers from 1 to 3.

3. A compound of claim 1 wherein R has from 12 to 26 carbon atoms.
4. A compound of claim 1 wherein R is
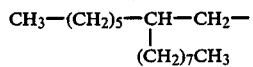
5. A compound of claim 1 wherein R is
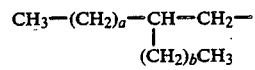
wherein a and b are integers from 6 to 17.
6. A compound of claim 1 wherein R is $CH_3-(CH_2)_{11}-$.
7. A compound of claim 1 wherein R is $CH_3-(CH_2)_{17}-$.
* * * * *